United States Patent [19]
Canadell et al.

[11] Patent Number: 5,207,676
[45] Date of Patent: May 4, 1993

[54] EXTERNAL FIXATOR WITH CONTROLLABLE DAMPING

[75] Inventors: José Canadell, Pamplona, Spain; Marcel H. Wagenknecht, Le Lignon, Switzerland; Juan Lazo de Zbikowski, Sevilla, Spain

[73] Assignee: Jaquet Orthopédie S.A., Geneva, Switzerland

[21] Appl. No.: 689,654

[22] Filed: Apr. 23, 1991

Related U.S. Application Data

[63] Continuation of Ser. No. 485,095, Feb. 26, 1990, abandoned.

[30] Foreign Application Priority Data

Feb. 27, 1989 [CH] Switzerland .................. 698/89-3

[51] Int. Cl.[5] ................................................ A61F 5/04
[52] U.S. Cl. ........................................ 606/54; 606/57
[58] Field of Search ................................ 606/54-58, 606/105

[56] References Cited
U.S. PATENT DOCUMENTS

| | | | |
|---|---|---|---|
| 4,312,336 | 1/1982 | Danieletto et al. | 606/57 |
| 4,488,542 | 12/1984 | Helland | 606/57 |
| 4,502,473 | 3/1985 | Harris et al. | 606/58 |
| 4,570,625 | 2/1986 | Harris et al. | 606/58 |
| 4,621,627 | 11/1986 | DeBastiani et al. | 606/57 |
| 4,848,368 | 7/1989 | Kronner | 606/57 |

*Primary Examiner*—Stephen C. Pellegrino
*Assistant Examiner*—Michael Rafa
*Attorney, Agent, or Firm*—Peter C. Richardson; Lawrence C. Akers; Elizabeth O. Slade

[57] ABSTRACT

This external fixator for the correction and reduction of bone fragments comprises a bar (1) fastened to a biocompression system (5), on which bar and system are disposed the supports (2,3) for fastening the pins inserted into the bones, the components of which supports are movable in accordance with the arrows A, B, C and D. The member (6) permits the longitudinal displacement of the clip (2) in the direction of the arrow E, while the biocompression system (5) makes a reciprocating movement in accordance with the arrow F.

A damping member (90,290) cooperates with means for regulating the force applied which are disposed outside the bar. Graduated markings (99,283) indicate the value of the force applied.

25 Claims, 3 Drawing Sheets

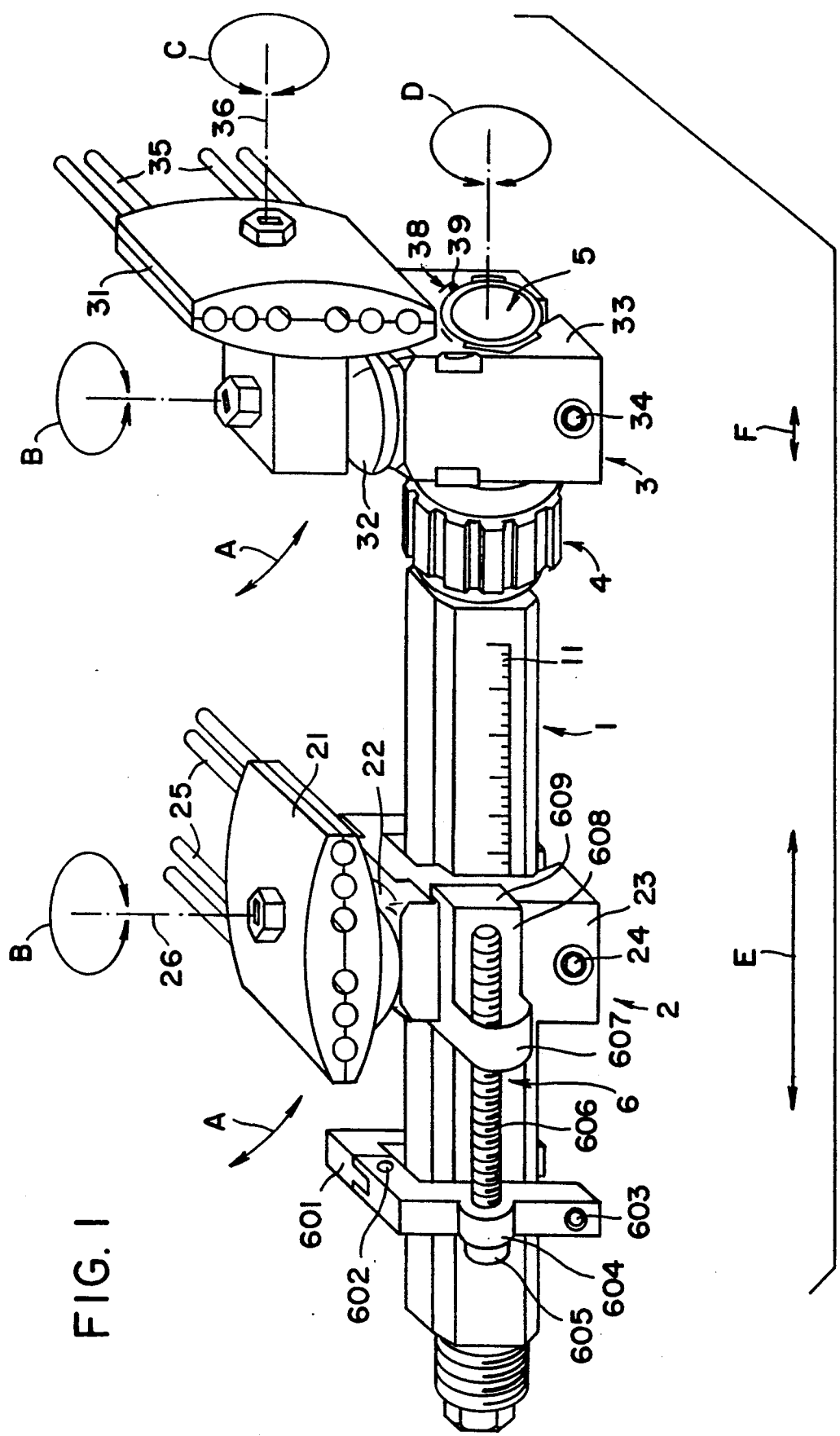
FIG. I

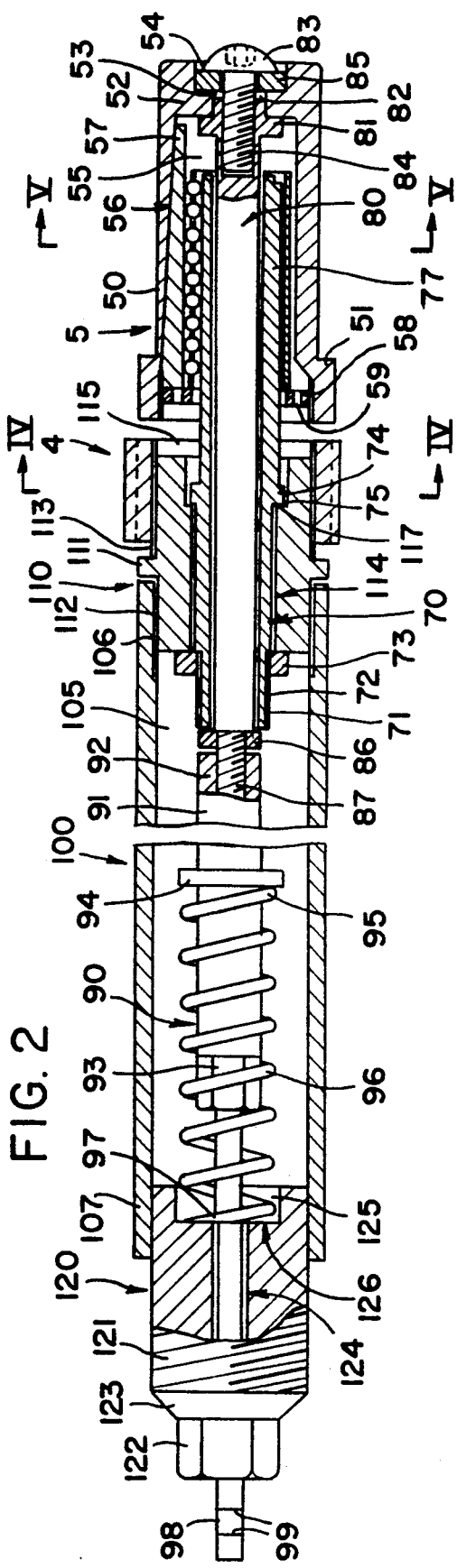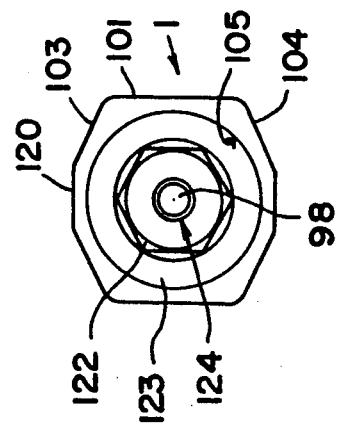

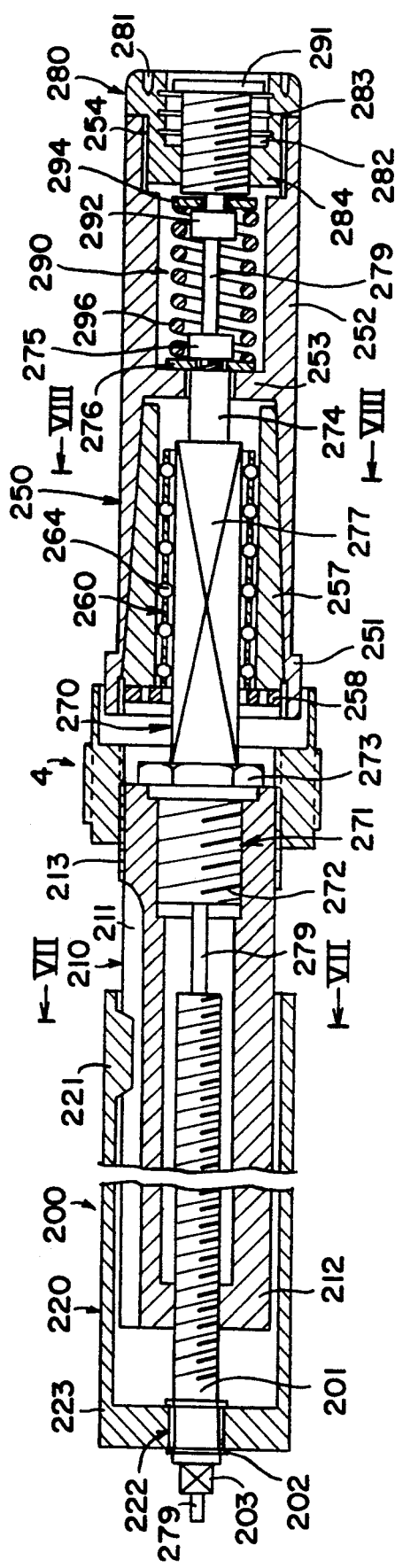
FIG. 6
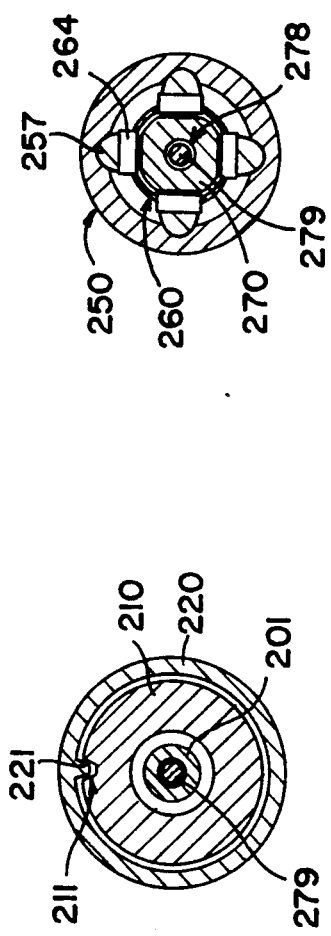
FIG. 8
FIG. 7

EXTERNAL FIXATOR WITH CONTROLLABLE DAMPING

This is a continuation of application Ser. No. 07,485,095, filed on Feb. 26, 1990 ABN.

The present invention relates to the field of traumatology and orthopedics and more particularly has as its object an external bone fixation device utilizing pins inserted into the bone.

By "traumatology" is understood casualty surgery and by "orthopedics" the correction of congenital malformations or malformations resulting from an incorrectly positioned bone union.

A number of devices permitting the elongation or compression of bones, whether or not a fracture or corticotomy exists, have been developed over a period of many years.

The invention relates to external fixators connected to sets of pins inserted into the bone and permitting longitudinal displacement of the sets of pins relative to the bone, while retaining their angular positions.

In this description reference is made to a fractured bone, but it is obvious that the bone may also be one intentionally cut through, for example for the purpose of orthopedic elongation. It may also be a bone which is not fractured or cut through, but the length of which it is desired to vary by compression or elongation, as is done in the case of young patients.

According to a technique which has been known for many years the pins are connected to an external fixation bar disposed substantially parallel to the fractured bone. Each set of pins inserted into a bone fragment is gripped in a support which can be oriented in relation to the fixation bar and which is fastened to a clip fixing it on the bar. In order to achieve the desired compression or elongation during the union of the bone it is possible either to displace one of the clips along the bar or to use a telescopic bar.

It is also known that in the course of the union of a bone it is advantageous to allow a slight reciprocating movement, known as biocompression, which enables the natural forces of the muscles and of the loads supported to act on the fracture, in order to stimulate the growth of the bone.

In U.S. Pat. No. 4,502,473 for example, an external fixator is described which has two sets of pins inserted into the bone and fixed to fastening clips, one of the pin fastening clips being movable along a fixation bar disposed parallel to the bone. An elastic member is provided in the part connecting the two clips and effects compression of the fracture over a limited path. In addition, this fixator can be equipped with pneumatic or mechanical means enabling passive stimulation to be achieved.

French Patent 2,517,195 (=U.S. Pat. No. 4,488,542) discloses a device for the correction and reduction of bone fragments, which comprises a rigid bar whose length is adjustable and on which are fixed two supports for pins inserted into the bone fragments. In a variant the longitudinal displacement is achieved through a telescopic movement between two polygonal tubes, of which one is fastened to a worm and the other to a nut. A sliding guide member is interposed between these two telescopic members to prevent any play and to allow frictionless sliding of one of the members relative to the other.

The present invention seeks to achieve control of the force applied on the relative displacement of the two sets of pins inserted into the bone fragments, in the case of either compression or elongation, in order to avoid damaging the callus being formed when the displacement force is applied.

The subject of the invention is an external fixator for the correction and reduction of bone fragments, which comprises a rigid bar disposed substantially parallel to the bone, at least two supports for the orientation of the pins inserted into the bone fragments, the distance between said supports being adjustable with the aid of a displacement member preventing any rotation between the supports, while the bar is provided with a member damping the longitudinal displacement.

It is characterized by the fact that:

a) the first support is fastened to a casing which is disposed at an end of the rigid bar and adapted to move relative to a sliding block fixed to the end of the bar, in such a manner as to obtain a reciprocating movement of the casing relative to the bar and to avoid any angular displacement;

b) the second support is displaceable longitudinally relative to the first one with the aid of said displacement member, and c) the damping member cooperates with damping force adjustment means disposed outside the end of the fixator.

Through the combination of the constructional members mentioned it is possible to obtain a fixation bar making it possible to displace a bone fragment throughout the bone union process without any risk of tearing the callus which is being formed, since the surgeon can ascertain the force applied at the time of the displacement, while in addition allowing a biocompression movement which assists the formation of the callus and is selected in dependence on factors personal to each patient.

In a preferred embodiment the sliding block has shapes intended to cooperate with corresponding cutouts in a connection member, in such a manner as to avoid any angular displacement. This sliding block has an end having a polygonal section and intended to slide, relative to the casing, in a needle bearing. Provision is advantageously made for the permitted length of longitudinal reciprocating movement to be limited in a predetermined manner.

The pin orientation supports consist of jaws disposed one on each side of the bar and cooperating with a curved deflection member adapted to permit the angular pivoting of clamps gripping the bone pins. Depending on requirements, an angle drive may be inserted between the curved deflection member and the clamp.

In a preferred embodiment the damping member consists of an elastic member compressed between two bearing surfaces, for example a coil spring, and means are provided for varying its compression. In order to enable the surgeon to ascertain the force applied, a rod adapted to project outside the bar is provided with graduated markings suitable for indicating values of forces.

In a known manner use will be made of a tubular bar of which one outer face carries graduations permitting measurement of the displacement made with the aid of the displacement member. In a preferred embodiment the bar has a generally quadrangular shape with edges cut off at 20° in order to effect the positioning of the pin orientation supports.

According to a first embodiment the displacement member adapted to effect the displacement of one of the supports consists of a displacement assembly disposed outside the bar and provided with means for fastening it to the bar and with means for the longitudinal displacement of said support.

In another proposed embodiment the displacement member adapted to effect the displacement of one of the supports consists of a device inside a bar consisting of telescopic tubes. This device may include a bevel gear unit in which one of the shafts can be driven from the outside, while the other shaft is fastened to a threaded rod adapted to cooperate with the telescopic tube which is to be displaced.

When the patient has to remain in bed, it is possible to use the external fixator described by adding to it a motor drive unit acting against the damping member and enabling biocompression movements to be simulated.

In order to reduce to the minimum the discomfort caused to the patient by the external fixator, it is endeavoured to reduce as much as possible the dimensions and weight of its components.

The accompanying drawings illustrate, by way of non-limitative examples, some embodiments of the present invention.

FIG. 1 is a schematic view in perspective of a first form of construction of an external fixator provided in addition with a device for the longitudinal displacement, along a fixation bar, of one of the clips fastening the pins inserted into a bone fragment.

FIG. 2 is a longitudinal section of the fixation bar and of the biocompression system which are shown in FIG. 1, taken on the lines II—II shown in FIGS. 4 and 5.

FIG. 3 is an end view of the free end of the fixation bar shown in FIG. 2.

FIG. 4 is a cross-section of the connection end of the fixation bar, taken on the line IV—IV in FIG. 2.

FIG. 5 is a cross-section of the biocompression system, taken on the line V—V in FIG. 2.

FIG. 6 shows in longitudinal section a variant form of construction of a fixation bar comprising telescopic members.

FIG. 7 is a cross-section on the line VII—VII of the fixation bar shown in FIG. 6.

FIG. 8 is a cross-section on the line VIII—VIII of the fixation bar shown in FIG. 6.

The general view given in FIG. 1 shows an external fixation bar 1 of polygonal section, on which are placed two clips 2 and 3 fastened indirectly to clamps 21 and 31 holding pins 25 and 35.

Each clip 2 or 3 is provided with a curved deflection member 22, 32 cooperating with a pair of jaws 23, 33 disposed one on each side of the bar 1, on which they are fixed by a positioning device 24, 34.

The curved deflection member 22 permits the angular pivoting of the clamp 21 in the direction of the arrow A, on the one hand, and the continuous orientation from 0° to 360° of the set of pins 25 relative to the clamping axis 26, in the direction of the arrow B, on the other hand.

The clip 3 is in addition provided with an angle drive means 37 enabling the clamp 31, and consequently the pins 35, to be turned 90°. An angle drive of this kind is for example used when the pins 35 are intended to be inserted into the epiphysis (for example the tibial or femoral head) of a bone whose diaphysis would receive the pins 25. In addition to the circular pivoting in the direction of the arrow A and the angular orientation in the direction of the arrow B, the clip 3 also permits angular orientation in accordance with the arrow C in relation to the axis 36 on which the pins 35 are clamped.

The arrow E represents the displacement of the clip along the bar, effecting the elongation or compression of the bone parallel to the bar, while the arrow F represents the limited biocompression movement, which is adjustable with the aid of the knurled nut 4 displaceable between the end of the bar 1 and the biocompression system 5, as will be seen in detail later on.

It should be noted that the biocompression system 5 is of generally cylindrical shape, thus also permitting the angular positioning of the clip 3 in the direction of the arrow D with the aid of an intermediate connection member 38, whose external shapes correspond to the internal cutouts of the jaws 33. The connection member 38 is also provided with an external collar 39 on each side of the clip 3, the purpose of which is to hold the connection member 38 in the clip.

The schematic view given in FIG. 1 also shows a member 6 for the displacement of the clip 2 along the bar 1, which may be provided with linear markings 11, usually graduated in millimeters.

The displacement member 6 consists of a fastening clip 601 composed of two parts articulated on an axis 602, and is clamped on the bar 1 by a screw 603. It also comprises a support 604 fixed for rotation with the clip 601 and having an opening for the retention of the head 605 of a feed screw 606, along which is moved a threaded boss 607 integral with a clamp 608 provided with two flanges 609 intended to embrace the side portion of the jaw 23 of the clip 2.

In the longitudinal section shown in FIG. 2 the external fixation bar 1 can be seen again under the reference 100. As already mentioned, it has a polygonal section, which is visible in the end view shown in FIG. 3, where it will be noted that the bar 100 has parallel faces 101 and 102, each followed by faces 103 and 104 inclined at 20° in such a manner as to provide optimum clamping of the bar in internal cutouts of corresponding shapes in the jaws of the clip. In a variant, a fixation bar of circular cross-section can be used, on which are clamped clips of corresponding shape.

The fixation bar 100 is tubular and has a circular central opening 105 terminating at each end of the bar in an internal screwthread 106 and 107 respectively.

The internal screwthread 106 receives a connection member 110 which is of generally cylindrical shape and has a median collar 111 serving as a stop on the one hand for the screwthread 112 making the connection to the fixation bar, or more precisely with the internal screwthread 106 of said bar, and on the other hand for the screwthread 113 intended to receive the knurled nut 4 previously mentioned.

The connection member 110 is provided with a circular central opening 114 ending externally in a recess 115 having at least one plane face 116 (more readily visible in FIG. 4), which is intended to prevent any rotation of the shaft passing through the opening 114. The recess 115 forms a stop shoulder 117 for said shaft which will be described in detail later on.

The internal screwthread 107 receives an adjusting end piece 120 of generally cylindrical shape, which has an external screwthread 121 matching the internal screwthread 107. The free end of the end piece 120 is provided with grip means, consisting for example of a hexagon 122 integral with the end piece 120 and following a frustoconical narrowed portion 123.

The adjusting end piece 120 has a circular central opening 124, in which a rod, the purpose of which will be mentioned later on, is slidable. The central opening 124 leads into a recess 125 forming a stop shoulder 126.

The biocompression system 5 previously mentioned in connection with FIG. 1 is shown in detail in longitudinal section and cross-section respectively in FIGS. 2 and 5.

It is composed of a casing 50 of generally cylindrical shape and provided at one end with an external collar 51 equipped with an internal screwthread, while the other end is closed by a wall 52 provided with a central passage 53 and an external recess 54. The casing 50 has a central opening 55 leading into four inclined cutouts 56 intended to receive four shims 57 each having a curvature corresponding to the cutouts 56 and also a longitudinally inclined plane face. The cutouts 56 are formed in such a manner that the plane faces of the shims 57 constitute the sliding faces of a needle bearing 60 provided with a cage 61 having a generally cylindrical shape and four external plane faces 62, along which are formed ladderlike cutouts 63 intended to receive the needles 64 constituting the needle bearing 60 (see FIG. 5).

The shims 57 and the needle cage 60 are held in the central opening 55 of the casing 50 by means of a washer 58 having an external screwthread intended to cooperate with the internal screwthread formed in the collar 51. The washer 58 is provided with cutouts 59 intended to receive a tightening tool of suitable shape.

Inside the needle cage 60 is disposed a sliding block 70 constituted by a tubular shaft having in succession:

an end 71 of circular section, provided with a screwthread 72 intended to receive a retaining nut 73;

a median collar 74 forming a stop shoulder 75 intended to cooperate with the stop shoulder 117 of the connecting member 110, the external contour of which collar is provided with flats 76 intended to engage against the plane faces 116 of the connecting member 110; and an end 77 of quadrangular section intended to slide in the needle cage 60.

The tubular shaft 70 has a central passage 78 of circular section, which is intended for the passage of a central shaft 80.

The central shaft 80 has at one end a collar 81 intended to bear against the inside of the wall 52, and its end 82 engages in the opening 53 in the casing 50, in which it is fixed by means of a screw 83 engaging in a central internally threaded opening 84 in the central shaft 80. In order to fasten the central shaft 80 in the casing 50 it is advantageous to dispose a washer 85 at the bottom of the external recess 54, thus in addition enabling the head of the screw 83 to be partly recessed.

The opposite end of the central shaft 80 to that where the biocompression system is disposed is provided with means for retaining the whole arrangement, consisting here of a nut 86 engaged on a terminal threaded portion 87 of the central shaft 80. The nut 86 is dimensioned to bear against the end 71 of circular section of the tubular shaft 70. The threaded portion 87 enables the connection to be made between the central shaft 80 and a means 90 the damping action of which is adjustable.

This damping means 90 consists of a rod 91 provided at one end with a central internally threaded opening 92 intended to cooperate with the threaded portion 87 of the central shaft. In order to make this connection the damping means 90 is provided with tightening means consisting, for example, of a hexagonal portion 93. Said rod is also provided with a median collar 94, against which bears the end 95 of a coil spring 96, whose other end 97 is received in the recess 125 and bears against the stop shoulder 126.

The means 90 ends in a rod 98 intended to slide in the central circular opening 124 in the adjusting end piece 120. The end of the rod 98 is provided with markings 99 the purpose of which will be mentioned later on.

In the embodiment illustrated in FIG. 6 the fixation bar is telescopic in order to permit the displacement, relative to one another, of the clips fastening the pins. Furthermore the damping means is disposed at the end of the casing.

In this variant the biocompressions system is found again composed of a casing 250 which receives in four inclined cutouts 256 shims 257 cooperating with the needles 264 of the bearing 260 intended to facilitate the reciprocating movement of the sliding block 270. The needle bearing 260 is disposed between the washer 258 threaded in the external collar 251 and an intermediate wall 253, while the damping member is located in the extension 252 of the casing, between said intermediate wall 253 and a plug 280 fixed in an internal screwthread 254 realized at the end of the tubular extension 252 of the casing.

The sliding block 270 presents:

an end 271 of circular section with an external screwthread 272 intended to cooperate with the end of the inner tube 210 of the telescopic bar 200, on which it is clamped through the hexagonal collar 273 (it is to be noted that this connection can be realized by equivalent means as gluing or soldering);

an end 274 of circular section intended to slide in a central opening of the wall 253, and having an internal screwthread intended to receive a screw 275 bearing on a washer 276;

an intermediate quadrangular section 277, intended to slide in the needle bearing 260.

Along its entire length the sliding block 270 may have a central opening 278 (FIG. 8) in which a shaft 279, the use of which will be mentioned later on, is slidable.

The plug 280 is provided with external cutouts 281 intended to receive a tightening tool for its fixation in the internal screwthread 254 realized at the end of the tube 253. The plug presents a central recess 282 having circular groves 283 intended to control the position of the damping member 290 (and consequently to measure the force applied), as well as an screwthreaded end wall 284 intended to receive the adjusting end-piece 291 for adjusting the force applied.

The damping means 290 is constituted by an external screwthreaded end-piece 291, having on its external face grip means, not represented in the drawing. The internal face of the end-piece 291 presents an internal screwthread intended to receive a screw 292 bearing on a washer 294. A spring 296 is situated between the washers 276 and 294, and its force can be adjusted by positioning the end-piece 291 in the plug 280.

In the embodiment of FIGS. 6 and 7, the fixation rod 200 is constituted by an inner tube 210 and an outer tube 220, of circular cross-section. As already mentioned, a graduated scale makes it possible to measure the relative displacement of the tubes. The tubes 210 and 220 are of aluminium. As an alternative, provision may be made for the inner tube to be formed by the superimposition of a stainless steel tube having a thin wall and an outer layer of carbon fibres, in order to reduce the weight.

To prevent any angular displacement of the tubes, the inner tube presents a fluting 211 in which slides a toe 221 of the outer tube. The relative movement of the tubes is obtained by means of a threaded shaft 201, maintained in a central hollow 222 of the outer tube wall 223 by means of two circlips 202 disposed in circular groves on each side of the wall 223. The already mentioned shaft 279 passes through the threaded shaft 201 and protrudes at its free end. Externally to the bar, the shaft 201 has grip means constituted by a squared end 203 or any other equivalent means. The threaded portion of the shaft 201 cooperates with a internal screwthread in the lateral wall 212.

As a variant, one can foresee not to turn the threaded shaft 201 at the end of the fixator, but to dispose a device with a bevel gear unit laterally along the bar, this unit having a drive gear fastened to grip means and a driven gear fastened to the threaded shaft 201.

The inner tube 210 is provided at the end receiving the biocompression system with an external screwthread 213 intended to cooperate with the previously mentioned knurled nut 4.

It should be noted that in order to simplify the drawing the clips and all the parts outside the fixation bar are not shown in FIG. 2 and subsequent figures.

For the well-being of the patient the various external components constituting the fixator according to the invention have no sharp edges and for the most part are made of light alloys in order to limit the weight of the apparatus.

Before being used in the course of the operation, the fixator according to the invention is assembled in the manner illustrated in the drawing. The biocompression casing 50 is assembled by inserting the shims 57 into the corresponding inclined cutouts 56, and then inserting the needle cage 60 surrounding the end 77 of quadrangular section of the sliding block 70, in the centre of which the central shaft 80 is disposed. The collar 81 disposed at the end of said shaft is pressed against the wall 52 by means of the screw 83 and the washer 85, in such a manner as to secure the central shaft 80.

This biocompression system thus formed is mounted at the end of an external fixation bar and its movement is facilitated by the rolling system in the needle cage 60.

In the embodiment shown in detail in FIGS. 2 to 5, the retaining nut 73 is tightened on the screwthread 72 in such a manner as to fasten the biocompression system to the external fixation bar, or more precisely to the connection member 110. The corresponding flats 116 and 76 of the connection member 110 and of the median collar 74 prevent any rotation between the fixation bar and the biocompression casing. The stop nut 86 is disposed on the threaded end portion 87 of the central shaft 80, in such a manner as to prevent the withdrawal of the biocompression system in the outward direction.

The internally threaded central opening 92 at the end of the rod 91 is screwed onto the threaded portion 87 with the aid of a tool matching the hexagonal portion 93. The coil spring 96 is placed in position on the rod 91, between the median collar 94 and the stop shoulder 126 on the adjusting end piece 120.

In the course of the actual operation the surgeon inserts sets of pins into each bone fragment, applying known techniques. Each set of pins 25 or 35 is held in a plane by means of the clamp 21 or 31 and is positioned relative to the bar 1 by taking advantage of the possible orientations in the directions of the arrows A, B, C and D (FIG. 1), which make it possible to dispose the bar parallel to the bone which is to be compressed or elongated. It is obvious that the angle drive device 37 is dispensed with in certain cases.

The clip 2 is disposed on the bar 1 with the aid of the positioning device 24 in such a manner as to be able to be displaced laterally by the displacement member 6, whose fastening clip 601 is clamped on the bar 1 with the aid of the screw 603.

The clip 3 is fastened to the biocompression system 5 through the tightening of the jaws 33 with the aid of the positioning device 34. It will be observed that by constructional measures it is easily possible to modify the relative angle between the two clips, since the clip 3 is mounted on a circular member, namely the biocompression casing 50, in order to allow adjustment in the direction of the arrow D in FIG. 1.

Throughout the bone union process the surgeon will be able to adjust the elongation or compression of the bone fragments by means of the feed screw 606 for the lateral displacement of the clip 2 in the direction of the arrow E.

He will also be able to adjust:

1) the biocompression stroke in the direction of the arrow F by acting on the knurled nut 4, which in FIG. 2 is shown in an intermediate position and which may either:

come into contact with the corresponding face of the casing 50, thus preventing any biocompression movement, or come to bear against the median collar 111, thus allowing a biocompression movement of the order of 5 millimeters;

2) the biocompression force by acting on the end piece 120, which enables the spring 96 to be compressed to a greater or lesser extent, the markings 99 on the rod 98 which slides in the central opening 124 in the end piece enabling this force to be measured. For this purpose, the markings correspond to values expressed in kilogram force.

A displacement of the clip 2 by 1 millimeter, which can be measured on the linear markings 11, corresponds to a displacement by 1 millimeter of the bone when equilibrium exists between the force of the spring 96 and the resistance of the patient's limb to elongation or compression. In case of elongation, it is to be noted that the damping means 90, through its spring 96, makes it possible to prevent the tearing of the callus being formed (anticollapse) at the moment when the clip 2 is displaced. As a rule a displacement of the order of 1 millimeter a day is made, but this value may vary in dependance on the age of the patient and other individual criteria, such as the rate of formation of the callus.

It is obvious that the feed screw 606 may be turned by automatic means, such as a drive motor, without departing from the scope of the present invention.

In the case of the second embodiment illustrated in FIGS. 6 to 8, its assembly is partly similar to that previously described, except that the damping member 290 is introduced in the casing 250.

In order to fasten the biocompression system to the external fixation bar, the casing 250 is tightened at the end of the inner tube 210, by means of the collar 273. The biocompression force is adjusted by means of the end-piece 291 and is measured on the marks 283 visible in the recess 282 beyond the end-piece 291.

The two telescopic tubes 210 and 220 are then joined together by inserting the threaded shaft 201. As already mentioned, the biocompression movements can be mechanically or electrically driven, in cases where the patient is confined to his bed. As an example the motor drive unit may consist of an electric motor turning an eccentric fastened to the free end of the shaft 279, which it drives in a reciprocating movement against the spring 296.

The telescopic fixation bar shown in FIGS. 6 to 8 is placed in position in the course of the operation, as indicated previously, and the fastening clips are clamped around the biocompression casing 250, on the one hand, and around the outer tube 220 of the telescopic tube 200, on the other hand.

In the course of the uniting of the bone the surgeon will be able to adjust the elongation or compression of the bone fragments by acting on the threaded shaft 201, ensuring the relative movement between the telescopic tubes 210 and 220.

It should be observed that the biocompression displacements are independent of the elongation or compression. As previously described, the amplitude of the biocompression movements is adjustable with the aid of the knurled nut 4.

As soon as a force is applied, in order to prevent the tearing of the callus being formed, any movement of one of the telescopic tubes relative to the other has the effect on the bone of a displacement different from that indicated on the graduated scale on the inner tube 210. It is in fact first necessary to balance the compression of the spring with the resistance reactions of the muscles and tissues, and only then will a relative displacement of the telescopic tubes by 1 millimeter result in an equivalent displacement of the sets of pins inserted into the bone.

It is obvious that the fixator according to the invention can be used to displace a bone segment between two parts of a long bone. In this case the fixator comprises two fixed supports and a displaceable support which is fastened to the bone fragment. It is further possible tu use some of the described components in a fixator maintaining the pins, without any compression or elongation of the bone.

Without going beyond the scope of the present invention it is of course possible to use the previously described fixation bar with ball joint type pin supports enabling the pins to be positioned in the desired plane and fastened on the one hand to the fixation bar and on the other hand to the biocompression casing.

We claim:

1. An external fixator for correcting and reducing fragments of a bone comprising in operable communication:
   a bar (1, 100, 200) to be disposed substantially parallel to the bone and having a longitudinal axis therethrough;
   a casing operatively connected to said bar for longitudinal movement with respect thereto;
   at least a first support (3) coupled to said casing and a second support (2) coupled to said bar for orienting pins to be inserted into said bone fragments;
   a displacement member (6, 201) acting between said bar and said second support for adjusting the distance between said first support and said second support and for preventing rotation between said first support and said second support;
   said casing is adapted to move relative to a sliding block (70, 270) fixed to said bar so as to obtain a longitudinal reciprocating movement of said casing with respect to said bar and so as to avoid angular displacement of said casing with respect to said bar;
   a damping member (90, 290) acting between said bar and said casing for damping the longitudinal displacement of said first and second supports;
   an adjustable stop mounted between said bar and said casing to limit the longitudinal movement of said first and second supports towards one another;
   said second support (2) is displaceable longitudinally relative to said first support by means of said displacement member (6, 201); and
   means for adjusting the damping action of said damping member.

2. An external fixator according to claim 1, wherein a portion of said sliding block (70, 270) has a polygonal cross-section (77, 277) intended to slide relative to said casing (50, 250).

3. An external fixator according to claim 2, wherein said polygonal cross-section (77, 277), slides in a needle bearing (60, 260) fastened to said casing and is adapted to facilitate reciprocating movement between said casing and said sliding block.

4. An external fixator according to claim 3, wherein said casing (50, 250) is provided with cutouts (56, 256) intended to receive shims (57, 257) having a curvature corresponding to the curvature of said cutouts (56, 256) and a plane surface adapted to cooperate with said needle bearing (60, 260).

5. An external fixator according to claim 4, wherein an end of said casing (50, 250) is provided with a collar (51, 251) having an internal screwthread adapted to receive a washer (58, 258) for securing said shims and said needle bearing in said casing.

6. An external fixator according to claim 1, wherein means (4) for adjusting the length of said reciprocating movement is provided between said casing (50, 250) and an end of said bar (100, 200) so as to limit said reciprocating movement.

7. An external fixator according to claim 1, wherein said first support and said second support (2, 3) comprise a first jaw and a second jaw (23, 22) disposed on each side of said bar (100, 200) and cooperating with a curved deflection member (22, 32) adapted to allow angular pivoting of clamps (21, 31) which grip said bone pins (25, 35).

8. An external fixator according to claim 7, wherein an angle drive (37) is inserted between said curved deflection member (22, 32) and said clamps (21, 31).

9. An external fixator according to claim 7, wherein an intermediate connection member (38) is disposed between said first jaw and said second jaw (23, 33) and said casing (50).

10. An external fixator according to claim 1, wherein said damping member (90, 290) comprises an elastic member compressed between a first bearing surface and a second bearing surface and wherein said first bearing surface (126, 276) is at least indirectly fastened to said bar and said second bearing surface (94, 294) is at least indirectly fastened to said casing.

11. An external fixator according to claim 10, wherein said damping member is a coil spring (96, 296).

12. An external fixator according to claim 10, wherein said first bearing surface (126, 276) is connected to an end-piece (120, 291) which is displaceable with respect to an element indirectly fastened to said casing (98, 280) provided with graduated reference markings (99, 283) adapted to indicate values of forces.

13. An external fixator according to claim 1, wherein said bar (100, 200) has a cross-section with a shape selected from the group consisting of circles and polygons.

14. An external fixator according to claim 13, wherein said bar (100, 200) has an outer face provided with graduations (11) making it possible to measure the movement effected by means of said displacement member (6, 201).

15. An external fixator according to claim 13, wherein said bar (100) has a generally quadrangular shape with edges cut off at about 20° so as to effect positioning of said pin orientation support (2).

16. An external fixator according to claim 1, wherein said bar (200) comprises an inner telescopic tube (210) and an outer telescopic tube (220).

17. An external fixator according to claim 16, wherein said displacement member adapted to effect displacement of a support comprises a threaded shaft non-rotatably mounted to one of said inner or outer tube (201, 210) and threadably engaging the other of said inner or outer tube.

18. An external fixator according to claim 17, wherein said displacement member adapted to effect displacement of a support comprises a displacement member (6) located outside said bar (100).

19. An external fixator according to claim 18, wherein said displacement member (6) is provided with means (601-603) for fastening said displacement member (6) to said bar and is provided with means (604-609) for longitudinal displacement of said support.

20. An external fixator according to claim 1, wherein said casing (50, 250) has an end wall (52, 252) at least indirectly fixed to a central rod (80, 279) adapted to slide in a central passage (78, 278) in said sliding block (70, 270) for ensuring a passive biocompression stimulation.

21. The external fixator as set forth in claim 1 further including a displacement member acting between said bar and said first support for adjusting the distance between said first support and said second support.

22. An external fixator for correcting and reducing fragments of a bone comprising:
a bar having a hollow interior defining a central longitudinal axis, said bar having a first support slidably mounted thereon for orienting bone pins to be connected to a first bone fragment;
a first tubular shaft extending along said axis rigidly mounted within said hollow interior and extending from an end thereof;
a second shaft slidably received within said tubular shaft for relative movement therebetween;
a casing slidably mounted on said first tubular shaft and rigidly connected to a first end of said second shaft, said casing having a second support for orienting bone pins to be connected to a second bone fragment; and
damping means acting between said bar and said second shaft along said longitudinal axis to dampen relative movement between said bar and said casing.

23. The external fixator as set forth in claim 22 further comprising an adjustable stop mounted between said bar and said casing to limit the movement of said casing towards said bar and said first and second supports towards one another.

24. The external fixator as set forth in claim 23 wherein said damping means is a coil spring surrounding a second end of said second shaft, a first end of said coil spring seated within a first end of said hollow interior of said bar and a second end thereof engaging said second shaft.

25. The external fixator as set forth in claim 24 wherein said adjustable stop is mounted at a second end of said hollow interior of said bar.

* * * * *